(12) United States Patent
Chatterjee et al.

(10) Patent No.: US 11,110,459 B2
(45) Date of Patent: *Sep. 7, 2021

(54) ASSAY WELLS WITH HYDROGEL AS A WELL-CONTENTS SEPARATOR

(71) Applicant: fannin partners llc, Houston, TX (US)

(72) Inventors: Dev Chatterjee, Saint Louis, MO (US); Leo Linbeck, III, Houston, TX (US); Michael John Heffernan, Katy, TX (US)

(73) Assignee: Fannin Partners LLC, Houston, TX (US)

( * ) Notice: Subject to any disclaimer, the term of this patent is extended or adjusted under 35 U.S.C. 154(b) by 251 days.

This patent is subject to a terminal disclaimer.

(21) Appl. No.: 16/188,329

(22) Filed: Nov. 13, 2018

(65) Prior Publication Data

US 2019/0091692 A1 Mar. 28, 2019

Related U.S. Application Data

(63) Continuation of application No. 15/793,490, filed on Oct. 25, 2017, now Pat. No. 10,195,609, and a
(Continued)

(51) Int. Cl.
*B01L 3/00* (2006.01)
*B01L 1/00* (2006.01)
(Continued)

(52) U.S. Cl.
CPC .......... *B01L 3/527* (2013.01); *B01L 3/50853* (2013.01); *B01L 3/502761* (2013.01); *B01L 3/54* (2013.01); *C12M 23/12* (2013.01); *G01N 21/78* (2013.01); *G01N 33/483* (2013.01); *G01N 33/5302* (2013.01); *G01N 33/54333* (2013.01); *B01J 2219/00317* (2013.01); *B01J 2219/00605* (2013.01); *B01L 2200/0647* (2013.01); *B01L 2200/0668* (2013.01); *B01L 2200/0673* (2013.01); *B01L 2200/0689* (2013.01); *B01L 2200/12* (2013.01); *B01L 2200/143* (2013.01); *B01L 2200/16* (2013.01); *B01L 2200/185* (2013.01); *B01L 2300/021* (2013.01);
(Continued)

(58) Field of Classification Search
CPC ....... C12M 23/12; C12M 23/34; C12M 25/16
See application file for complete search history.

(56) References Cited

U.S. PATENT DOCUMENTS 5,229,163 A * 7/1993 Fox ...................... B01L 3/50853
204/169
2011/0008813 A1* 1/2011 Dilleen ............. B01L 3/502715
435/28
(Continued)

*Primary Examiner* — Nathan A Bowers
(74) *Attorney, Agent, or Firm* — Eric P. Mirabel

(57) ABSTRACT

In a polymer assay cartridge having wells containing reagents, beads and sample, where the wells are covered (e.g., with Parafilm® or films) and shipped to the point of care, the reagents and well contents can leak out. The reagent solutions are made semi-solid by adding hydrogel reagents and cooling to form a gel. Preferably, the hydrogel is heated before an assay is conducted with the cartridge, and pigmented beads in the wells indicate melting or excessive heating, or congealing of the hydrogel, based on pigment color change.

17 Claims, 13 Drawing Sheets

Related U.S. Application Data continuation-in-part of application No. 15/793,445, filed on Oct. 25, 2017, now Pat. No. 10,126,297, and a continuation-in-part of application No. 15/793,384, filed on Oct. 25, 2017, now Pat. No. 10,828,636.

(60) Provisional application No. 62/412,751, filed on Oct. 25, 2016, provisional application No. 62/412,745, filed on Oct. 25, 2016, provisional application No. 62/412,761, filed on Oct. 25, 2016, provisional application No. 62/412,769, filed on Oct. 25, 2016, provisional application No. 62/412,734, filed on Oct. 25, 2016.

(51) Int. Cl.
*G01N 33/483* (2006.01)
*C12M 1/32* (2006.01)
*G01N 21/78* (2006.01)
*G01N 33/53* (2006.01)
*G01N 33/543* (2006.01)

(52) U.S. Cl.
CPC . *B01L 2300/069* (2013.01); *B01L 2300/0816* (2013.01); *B01L 2300/0887* (2013.01); *B01L 2400/043* (2013.01); *B01L 2400/0677* (2013.01)

(56) References Cited

U.S. PATENT DOCUMENTS

| | | | |
|---|---|---|---|
| 2012/0020850 A1* | 1/2012 | Sommer | B01L 3/50853 422/430 |
| 2014/0057271 A1* | 2/2014 | Kelso | C12N 15/1006 435/6.12 |
| 2014/0357511 A1* | 12/2014 | Handique | G01N 33/57423 506/9 |
| 2016/0096175 A1* | 4/2016 | Pallas | C12Q 1/686 506/7 |

* cited by examiner

ASSAY WELLS WITH HYDROGEL AS A WELL-CONTENTS SEPARATOR

RELATED APPLICATIONS

This application is a continuation of U.S. application Ser. No. 15/793,490, filed Oct. 25, 2017 (which claims priority to Provisional Application Nos. 62/412,745; 62/412,761; and 62/412,751, all filed Oct. 25, 2016) and also claims priority to U.S. application Ser. No. 15/793,445, filed Oct. 25, 2017 (which claims priority to Provisional Application No. 62/412,734, filed Oct. 25, 2016), and to U.S. application Ser. No. 15/793,384, filed Oct. 25, 2017 (which claims priority to Provisional Application No. 62/412,769, filed Oct. 25, 2016).

GOVERNMENTAL RIGHTS

This invention was made with governmental support under Grant Numbers 1R43DA041966-01; and 1R43DA043325-01, both awarded by the National Institute on Drug Abuse. The government has certain rights in the invention.

BACKGROUND

A reliable, robust assay system which can be deployed to a point of care is useful in a number of settings. For example, where there is an infectious disease outbreak in a remote area (e.g., the recent Ebola outbreaks), such an assay is of benefit for arresting the outbreak as quickly as possible (infected individuals can be quickly located then isolated) and for keeping health care providers safer.

An assay driver system can be used to automate an assay. One type of assay driver induces movement of magnetic beads which contact sample (or control) and then carry it into contact with assay reagents. The movement has to be carefully timed, to ensure proper reaction times in different reagents. The results must also be readable for fast interpretation. One type of discontinuous point of care assay system with an assay driver suitable for use herein is disclosed in US Publ'n No. 2017/0102384 (incorporated by reference). This application discloses a substantially transparent cartridge having wells containing various assay reagents. Magnetic beads also reside in the wells, and the magnetic beads are moved among the wells in order to carry sample into contact with different assay reagents in different wells. It also discloses that a preferred material for sealing one side of the cartridge, in a manner such that only the channels connecting the wells are open to the outside, and the open side of the wells are sealed, is a translucent plastic paraffin film, including but not limited to Parafilm®. It is noted that the magnetic beads will be attracted towards the paraffin film during the assay, and will move along its inside surface during their movement among the wells. The inner side of paraffin film allows such movement. The assay is more user-friendly for point of care use, if it is shipped to the point of care with the magnetic beads and assay reagents (and preferably, control solution) loaded in the wells—leaving only sample for the point of care operator to load. The other side of the cartridge, with the openings for the channels, can be sealed with tape or other material—for shipment or storage. The tape may or may not be needed to be removed to conduct the assay at the point of care.

Even with both sides of the cartridge sealed (by tape on one side and a preferred material on the other), the reagents, magnetic beads or other materials in the wells may tend to migrate out of the wells or into the channels during transport. It is desirable to stop such potential migration, so all items start in the appropriate well when the assay is conducted at the point of care. If a gel is used to maintain materials in wells, it is useful to have a temperature indicator associated with the assay, so the temperature at which the gel melts—whereupon reagents, magnetic beads or other materials can be moved among wells during the assay—is indicated.

SUMMARY

The migration of reagents among wells and into channels during transport of a loaded assay cartridge can be prevented or inhibited by substantially increasing the viscosity of the reagent solutions. One type of material which is suitable for such purpose is gelatin hydrogel, which is non-reactive with most reagents. In use, it is mixed with the reagent solutions in the wells.

Preferably, a gelatin hydrogel is selected which is semi-solid at room temperature and below (i.e., during shipment) but which is melted to liquefy the reagent solutions at the time of the assay. The liquification temperature for the gelatin hydrogel should be lower than that which affects the reagents or any assay activity, and lower than the melting point of the paraffin coating of the Parafilm® (or other plastic paraffin films or portions of the assay kit).

Some gelatin hydrogels have a melting temperature (i.e., transition from solid to liquid) higher than their gelling temperature (i.e., transition from liquid to solid)—which is known as hysteresis. The preferred hydrogels are selected such that the hydrogel-reagent solution has a melting temperature (following gelling) above that encountered during shipment. Melting of the gelatin (i.e., failure to maintain a gel) could result in leakage of materials in the wells during shipment. During manufacturing, the hydrogel-reagent solution is preferably heated to melting so that reagent solutions can be conveniently placed or injected into the wells of the cartridge in liquid form, followed by cooling to gel it, before shipment. Among factors affecting the melting/gelling temperature is the concentration of the hydrogel in the solution—where a higher concentration is associated with a higher melting and gelling temperature.

In one embodiment, the hydrogel-reagent solution melts below room temperature (RT), so the cartridge can be shipped at refrigeration temperature (about 4° C.), and then warmed to room temperature just prior to beginning the assay. However, such characteristics are difficult to achieve. Instead, suitable solutions were made with a melting temperature at about 37° C. and a gelling temperature slightly above the range of refrigeration temperatures (around 10° C. to 15° C.). With these solutions, after heating to melting once and loading the assay wells, the temperature is reduced to about 4° C. to cause gelling of the hydrogel-reagent solution. The cartridge is preferably stored and shipped at 4° C. (which is typically a suitable temperature for storage of assay reagents), and the hydrogel-reagent solution remains gelled during shipment. Because the melting temperature is about 37° C., the cartridge can tolerate temporary temperature excursions (even up to room temperature, or 25° C.) and maintain the gel state. Before the assay is run, the hydrogel-reagent solution must again be heated to melting—so the reagents are in solution. The melting temperature is low enough to not negatively affect reagents or assay performance.

The Bloom number is a measure of the gel strength of gelatin, reflecting the average molecular weight of its constituents. Gels in commerce can range up to 300 Bloom. Gels in foods usually range from 125 to 250 Bloom. Preferred gelatin hydrogels for use in the invention include high Bloom at 1% concentration, as such higher Bloom numbers were found to provide better control over melting and gelling points.

The Parafilm® (or other plastic paraffin films used as the sealing material) can be adhered to the polymer cartridge, which is normally molded with a smooth finish in the regions between wells, by roughening the normally-smooth polished portions where the sealing material contacts, or by using a mold which produces a cartridge with such roughened regions. More preferably, these portions of the surface have SPIB-1 grade finish, or approximately a 600 grit finish.

BRIEF DESCRIPTION OF THE DRAWINGS

FIG. 1 is a perspective view of an assay cartridge from the side that the wells open to.

Figure 1:
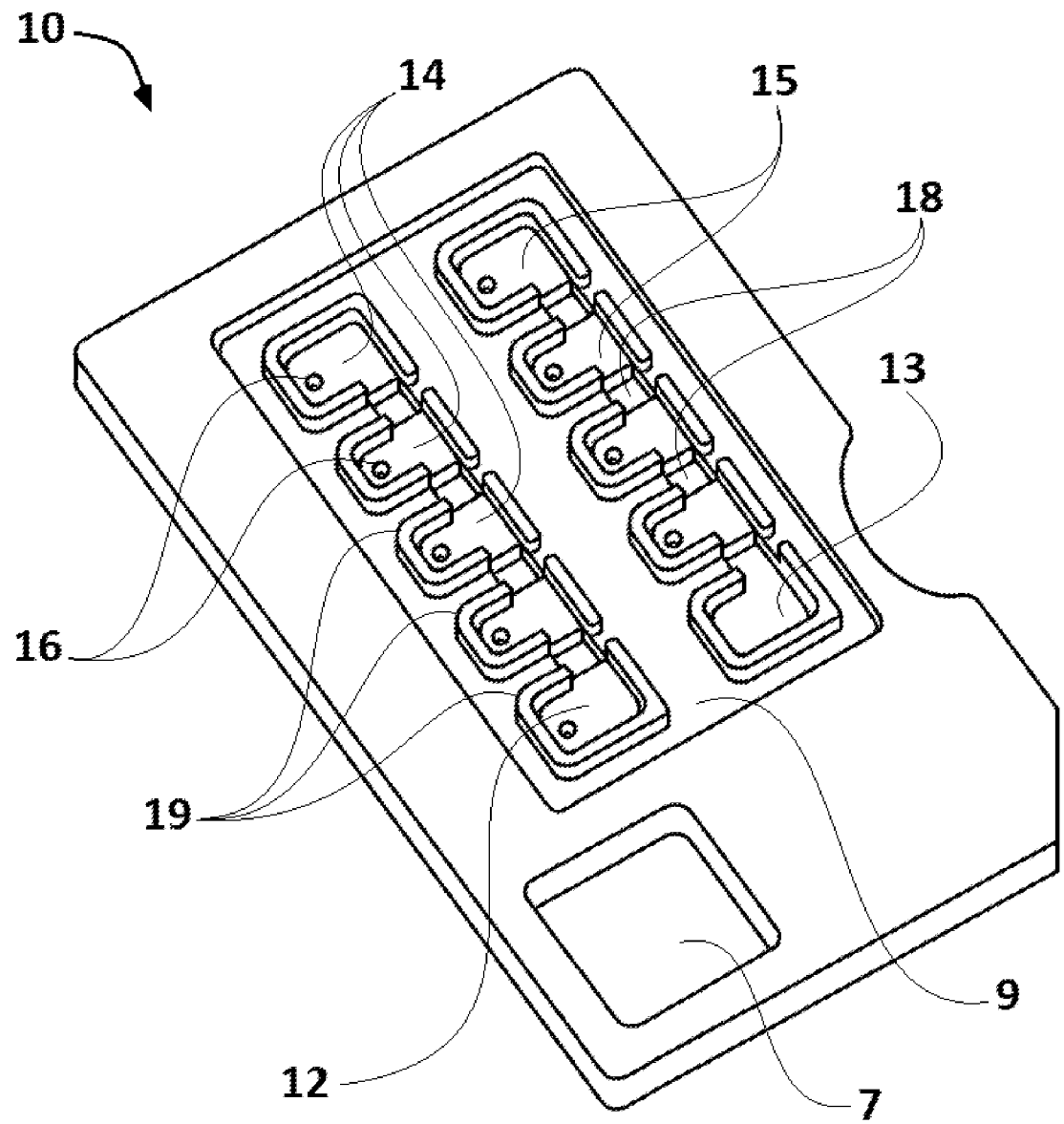
Figure 2:
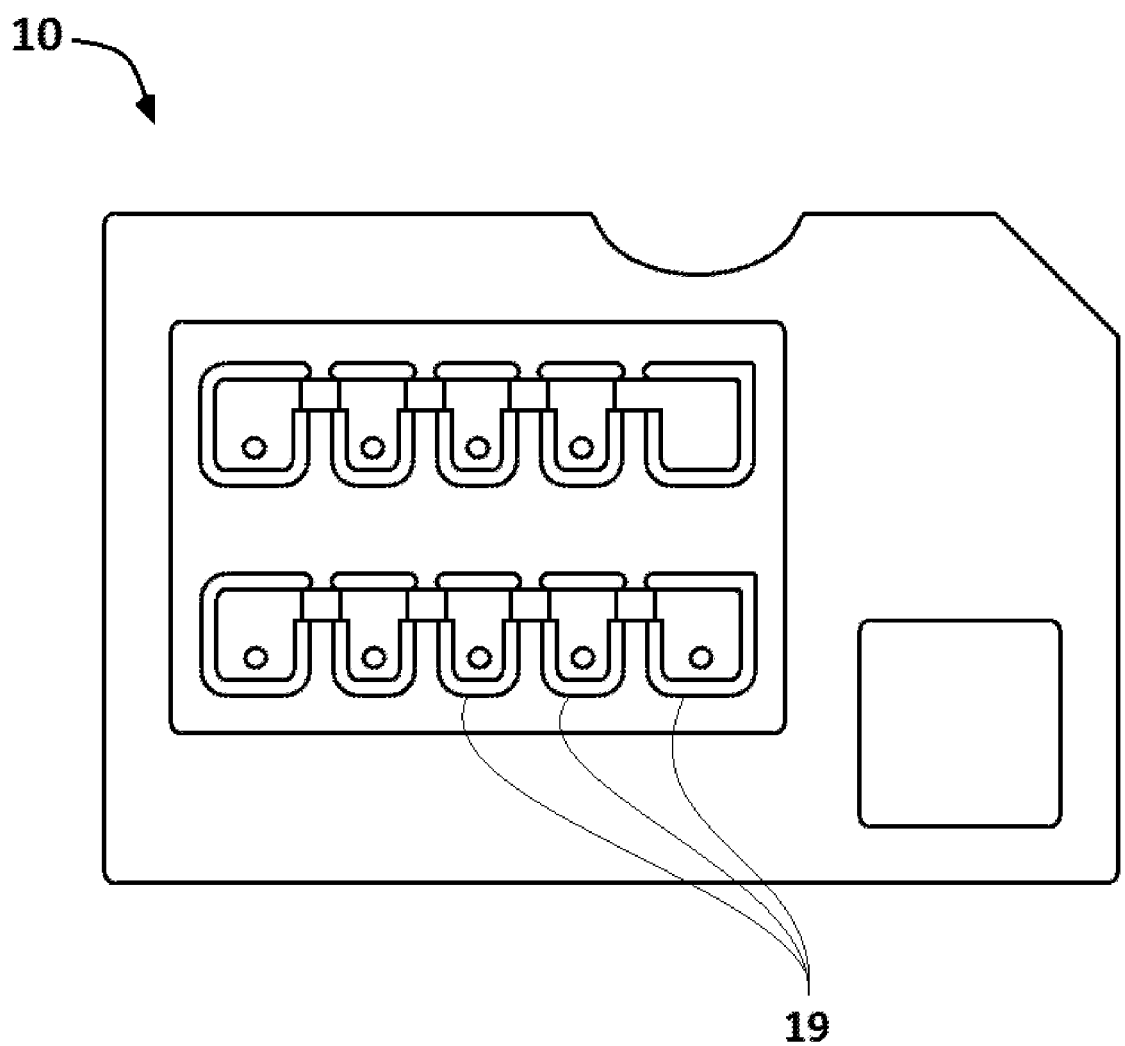
FIG. 2 is a plan view of the assay cartridge of FIG. 1.
Figure 3A:
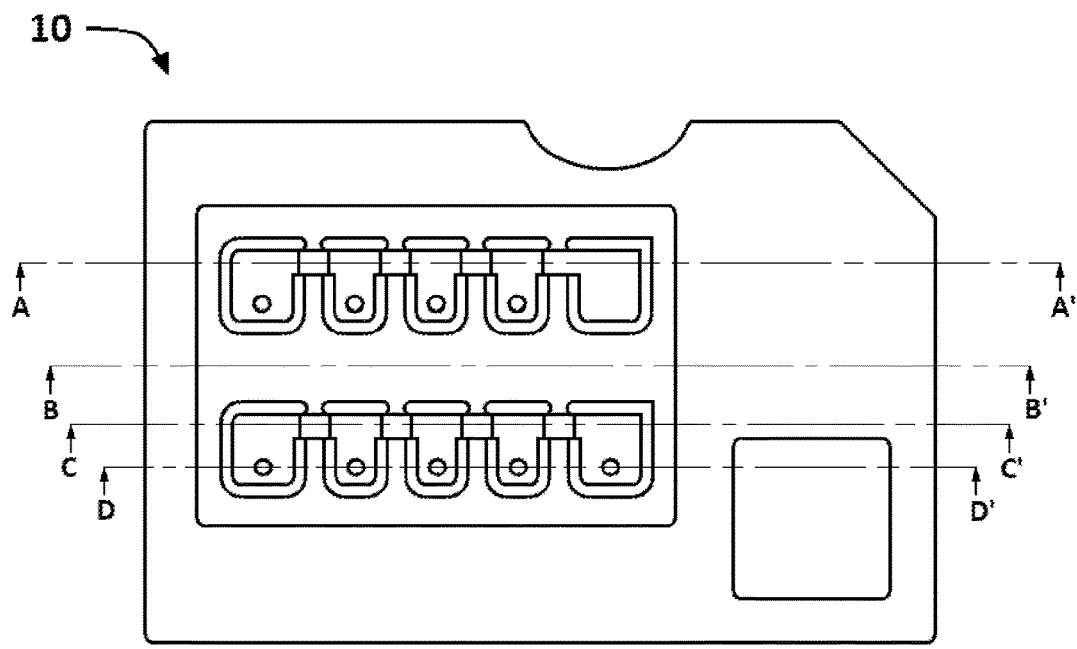
FIG. 3A is a plan view of the assay cartridge of FIGS. 1 and 2.
Figure 3B:
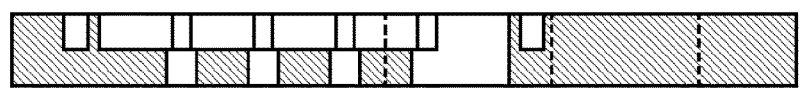
FIG. 3B is a sectional view of the assay cartridge of FIG. 3A taken along the lines A-A'.
Figure 3C:
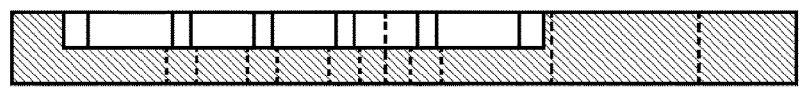
FIG. 3C is a sectional view of the assay cartridge of FIG. 3A taken along the lines B-B'.
Figure 3D:
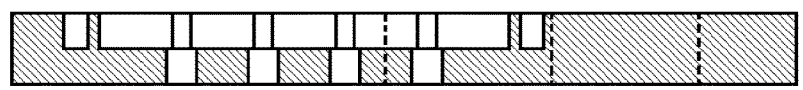
FIG. 3D is a sectional view of the assay cartridge of FIG. 3A taken along the lines C-C'.
Figure 3E:
FIG. 3E is a sectional view of the assay cartridge of FIG. 3A taken along the lines D-D'.

It should be understood that the drawings and the associated descriptions below are intended only to illustrate one or more embodiments of the present invention, and not to limit the scope of the invention. The drawings are not necessarily to scale.

DETAILED DESCRIPTION

Definitions

The term "magnetic beads" refers to bead-shaped objects of any size (including microbeads) and composition which can be attracted or repulsed by a magnetic force, including objects containing paramagnetic materials or magnetizable materials, such as conductors, and including conductive metals.

"Plastic paraffin film" includes but is not limited to Parafilm® and any other product having the recited features.

"Grit finish" and "600 grit finish" include SPIB-1 grade finish and any other finishes having the recited features.

Referring to FIGS. 1 to 3E, a preferred embodiment of an assay cartridge 10, is shown. Assay cartridge 10 has two rows of a series of wells, with the first well in each row labeled as 12 and 13 respectively, and the remaining wells in one row designated 14, and the remaining wells in the other row designated 15. Each well (12, 13, 14, 15) also has a mini-hole 16. Assay cartridge 10 also has a series of channels 18, which extend completely through the cartridge 10, and separate each well (12, 13, 14, 15) from the well next to it. In this preferred embodiment, there is a depressed section 9 of the cartridge, a hole 7 in corner, and ridges 19 around the periphery of a substantial portion of each of the wells (12, 13, 14, 15). Ridges 19 function to direct capillary flow around each of the ridges, and to prevent fluid from readily migrating between wells.

FIGS. 5A to 5C, and 5E, show a transparent or translucent layer 20 (preferably a plastic paraffin film, including but not limited to Parafilm® and similar products, which are transparent or translucent and can adhere to cartridge 10) covers and seals the wells of the related cartridge embodiment 11 (which does not include hole 7, depressed section 9 or ridges 19). Layer 20 is also designed to adhere to the portions of cartridge 10 outside section 9 and to the upper surfaces of ridges 19, to seal the contents of the wells 12, 13, 14, 15 and one side of the channels 18 (and hole 7) from the surroundings. With translucent layer 20 in place, channels 18 form air gaps between adjacent wells 12, 13, 14, 15 of cartridge 10 (or cartridge 11).

The Parafilm® (or other plastic paraffin films) can be adhered to the appropriate portions of polymer cartridge 10 (or 11) by roughening the normally-smooth polished portion of the cartridges' surface where the film contacts. More preferably, these portions of the surface have approximately 600 grit finish, and suitable finishes include SPIB-1 grade finish. Alternatively or with such a finish, one could assist in adhering the film to the cartridge using heat and/or pressure, including preferably by using a roller laminator to apply pressure and/or heat.

Alternatively, one could do away with Parafilm® and instead use a liquid adhesive on a backing. The liquid adhesive is then spread over the backing e.g., by heating to reduce the viscosity. The backing can be the imprinted with a readable code 5 (see below), and then spread, e.g., by heating and blowing air, across the backing. To adhere the backing to the cartridge 10 or 11, the adhesive on the backing is contacted with the cartridge 10 or 11.

Cover 22 is designed to protect layer 20, especially during transport. Cover 22 is preferably paper or polymer or other material which can be imprinted with a carries a QR code, other readable code, or a barcode 5, and which provides a consistent background color for the last wells (14, 15) wherein a color change takes place (see below), and, in some cases, it may be removed from layer 20 before cartridge 10 or 11 is used in an assay. Readable code 5 is preferably printed on the inner side of cover 22, so that it can be seen or scanned from at least one side when cover 22 is in place on cartridge 10 or 11.

In one example of running an ELISA assay with cartridge 10, sample solution is introduced into well 12, and a control solution is introduced into well 15. Preferably, the sample and control are loaded through the mini-holes 16 in the respective wells. Magnetic microbeads coated with antibody against antigens in the control (and which may target antigens in the sample, if the sample is positive) are placed into mini-holes 16 in the wells 14 and 15 which are nearest to wells 12 and 13.

Reagents for other steps in the assay (e.g., solutions of labeled detection antibodies which target and bind to the antigens; solutions to develop the labels on the detection antibodies into discernable colors) are placed into the mini-holes 16 of other wells 14 and 15. These reagents are placed in wells 14 and 15 in a series such that the requisite assay steps are performed as the magnetic beads are moved from the wells they first reside in, then to wells 12 and 13 (where some contact sample and some contact control) and then through the series of wells 14 and 15.

The wells (12, 13, 14, 15) are then sealed with layer 20, and layer 20 is preferably covered by cover 22. The combined thickness of layer 20 and the cover 22 is preferably about 100 to 500 microns—though the combined thickness can vary, with the controlling parameter being the need to keep the magnets (see below) which act on magnetic beads in the wells during an assay, a specified distance from the magnetic beads.

Figure 4A:
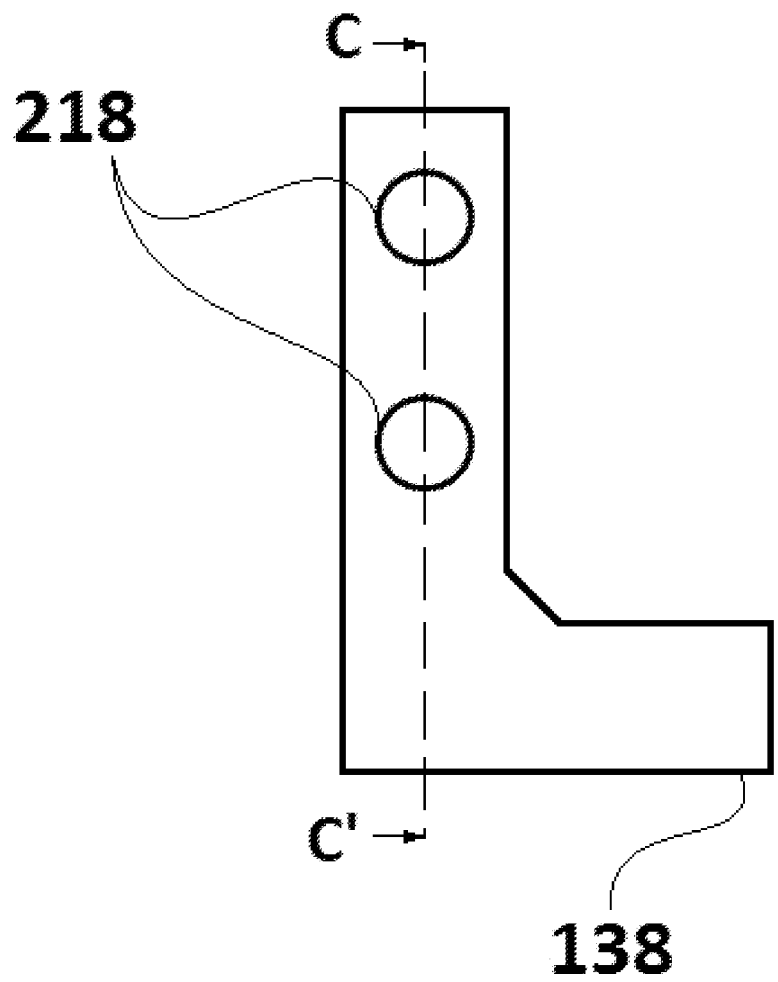
FIG. 4A is a plan view of a magnet holder.
Figure 4C:
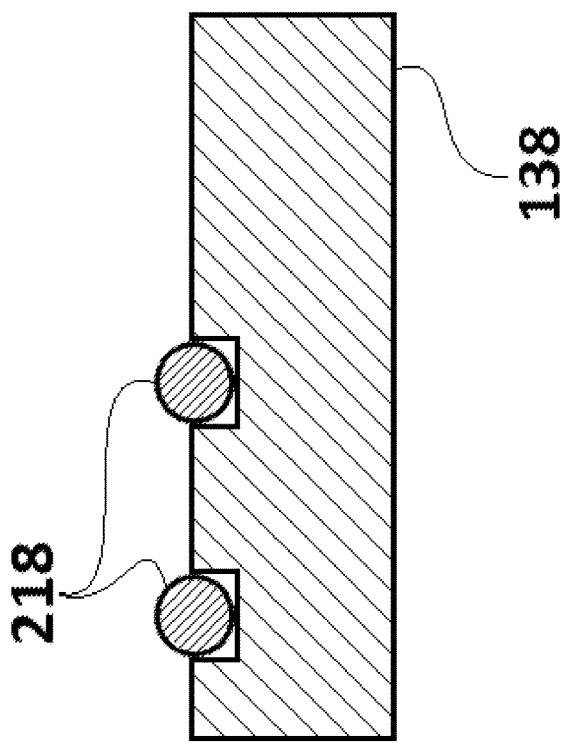
FIG. 4C is a cross-sectional view of another embodiment of the magnet holder of FIG. 4A, taken along line C-C'.
Figure 4B:
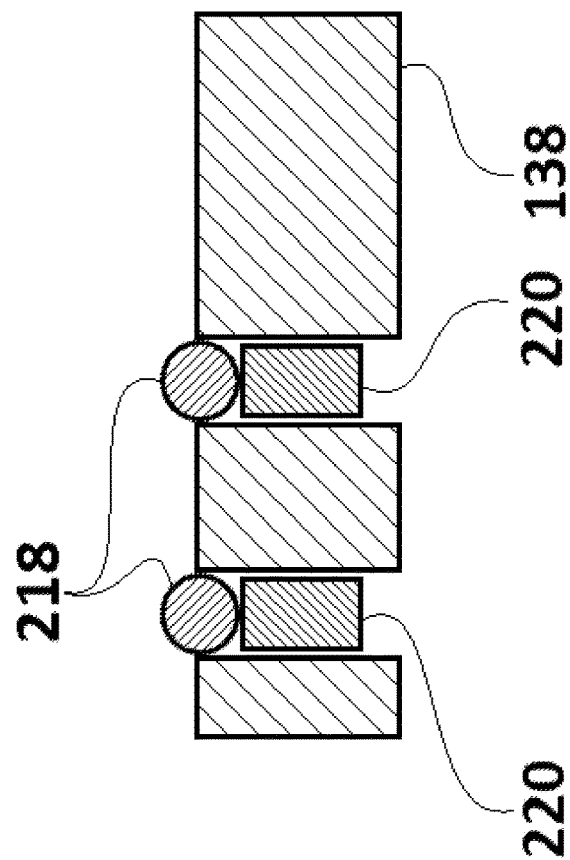
FIG. 4B is a cross-sectional view of one embodiment of the magnet holder of FIG. 4A, taken along line C-C'.
Figure 5A:
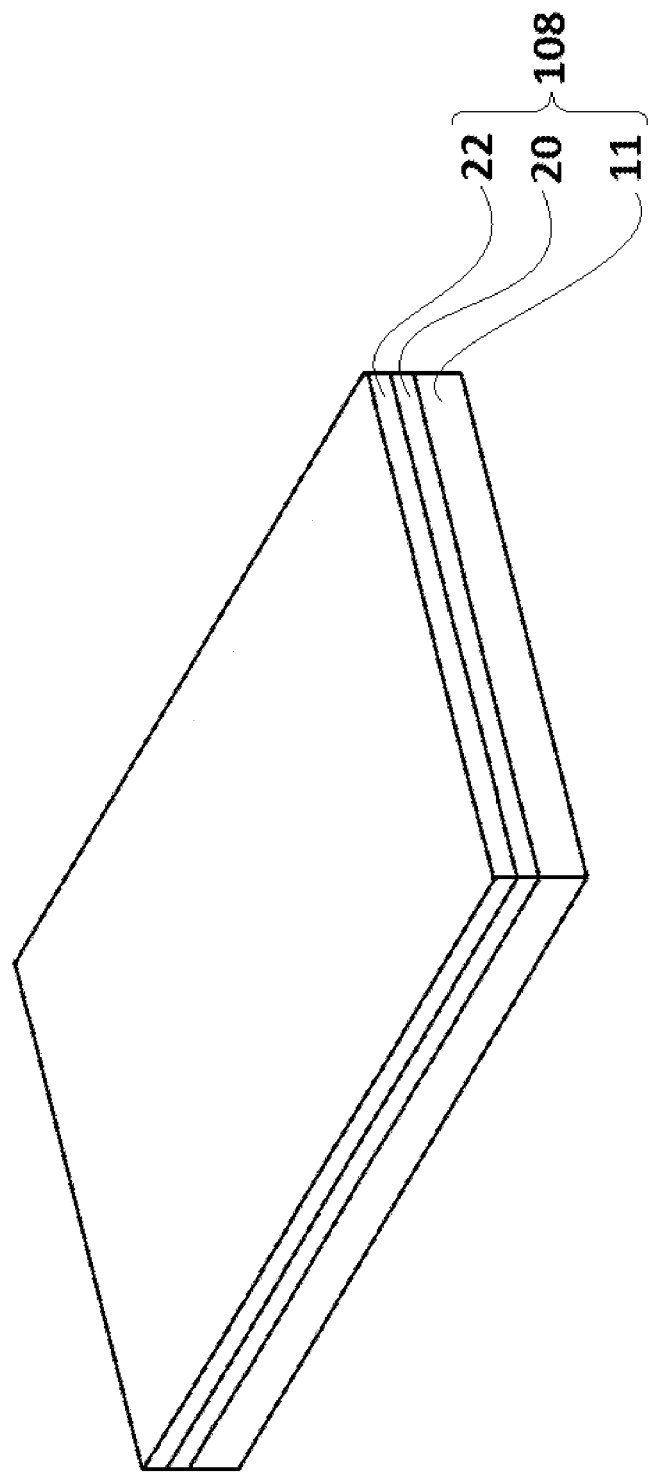
FIG. 5A is a perspective view of an assay cartridge assembly with a first layer and a protective cover layer in place.
Figure 5B:
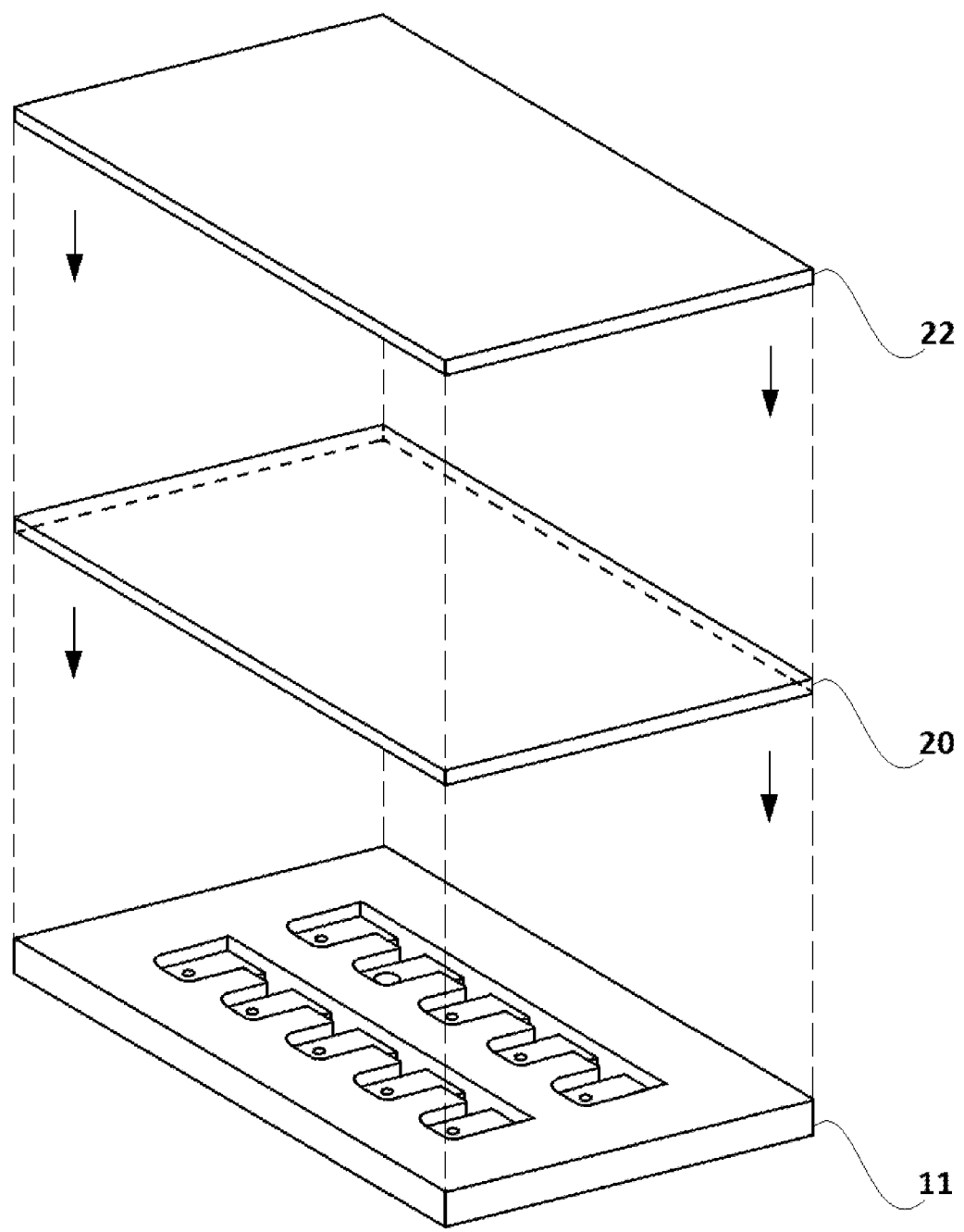
FIG. 5B illustrates an exploded view of a first layer and a cover layer, which are both suitable for covering the assay cartridge shown in FIGS. 1 to 3E (though a related embodiment of the assay cartridge is shown in FIG. 5B).
Figure 5C:
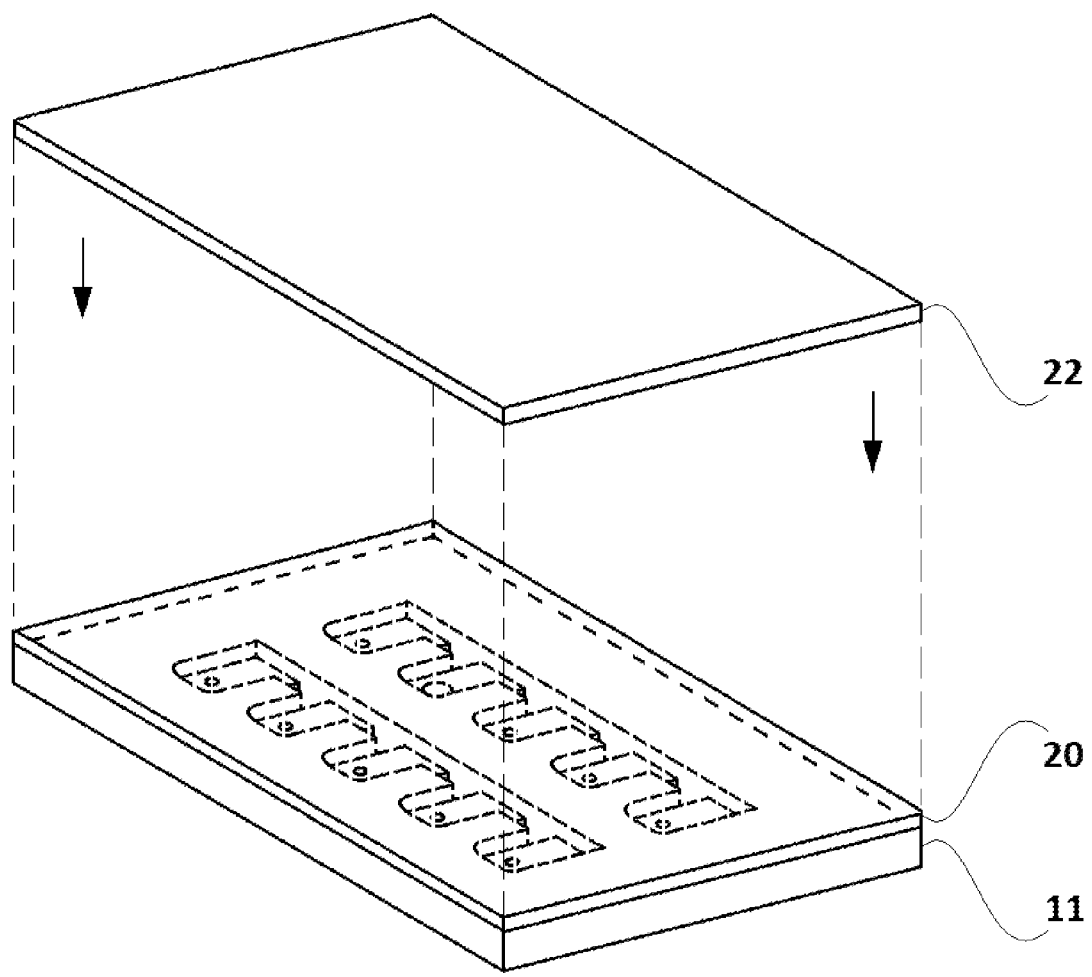
FIG. 5C illustrates a perspective view of the assay cartridge assembly shown in FIG. 5B with the first layer in place and the cover separated.
Figure 5D:
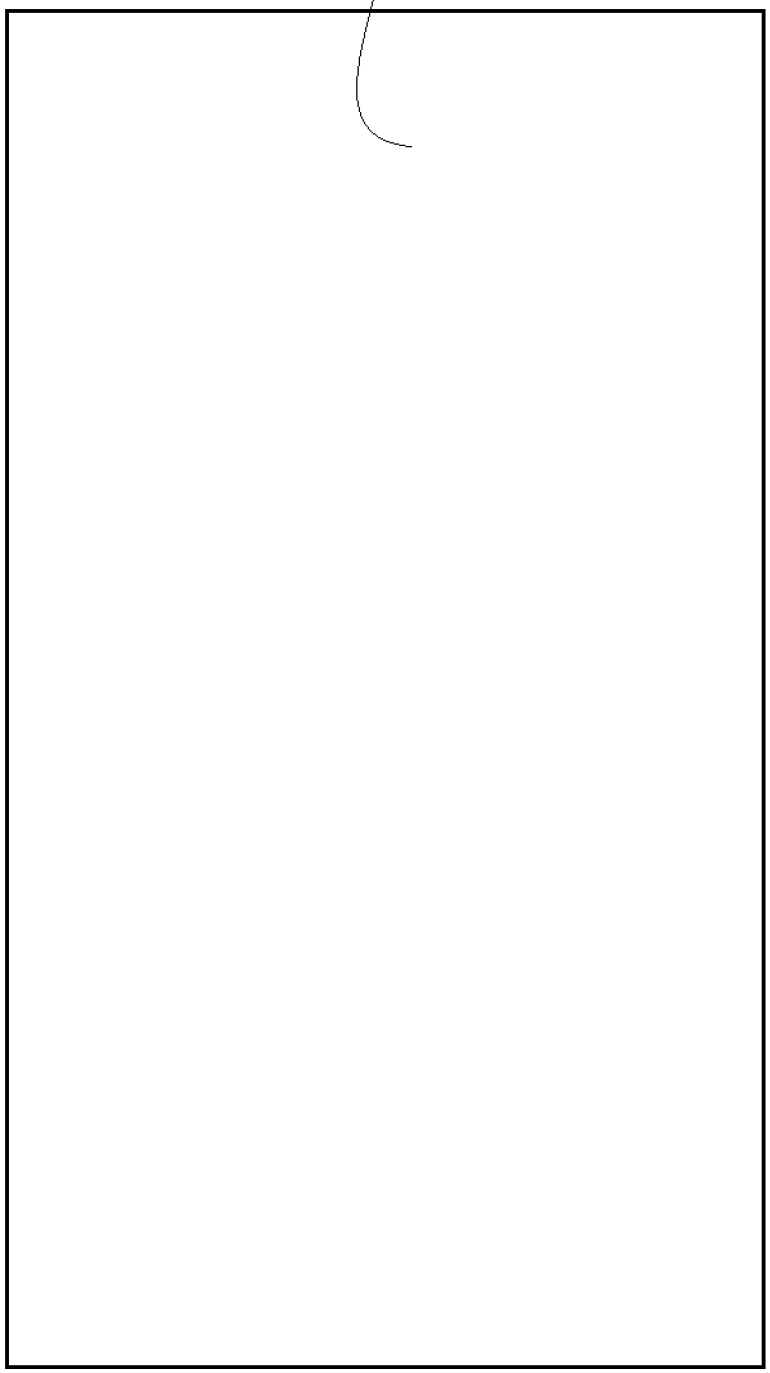
FIG. 5D illustrates a plan view of one side of the assay cartridge shown in FIG. 5B with the cover in place.
Figure 5E:
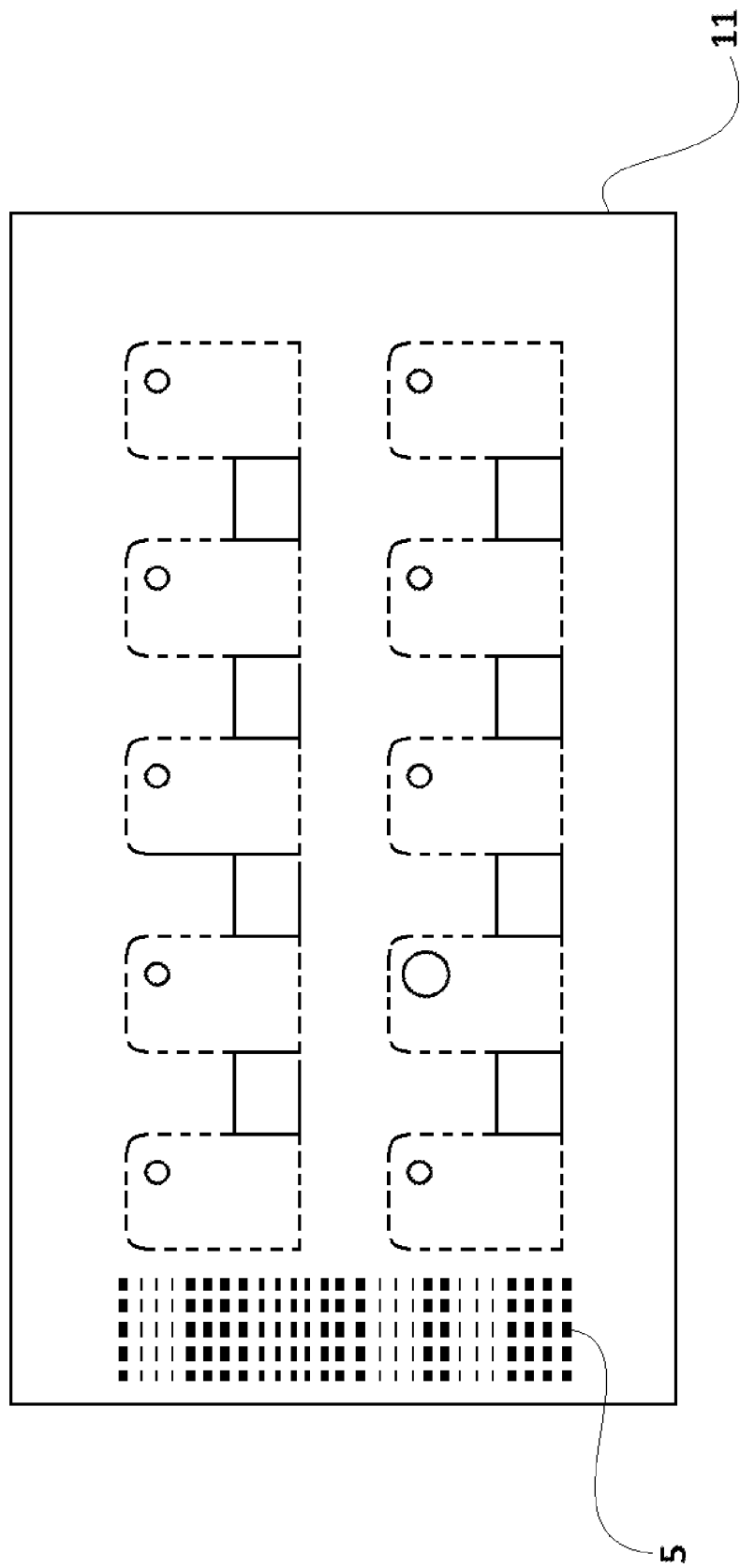
FIG. 5E illustrates the view of the side of the assay cartridge shown in FIG. 5D, where the cover layers are made partially transparent for illustration.
Figure 5F:
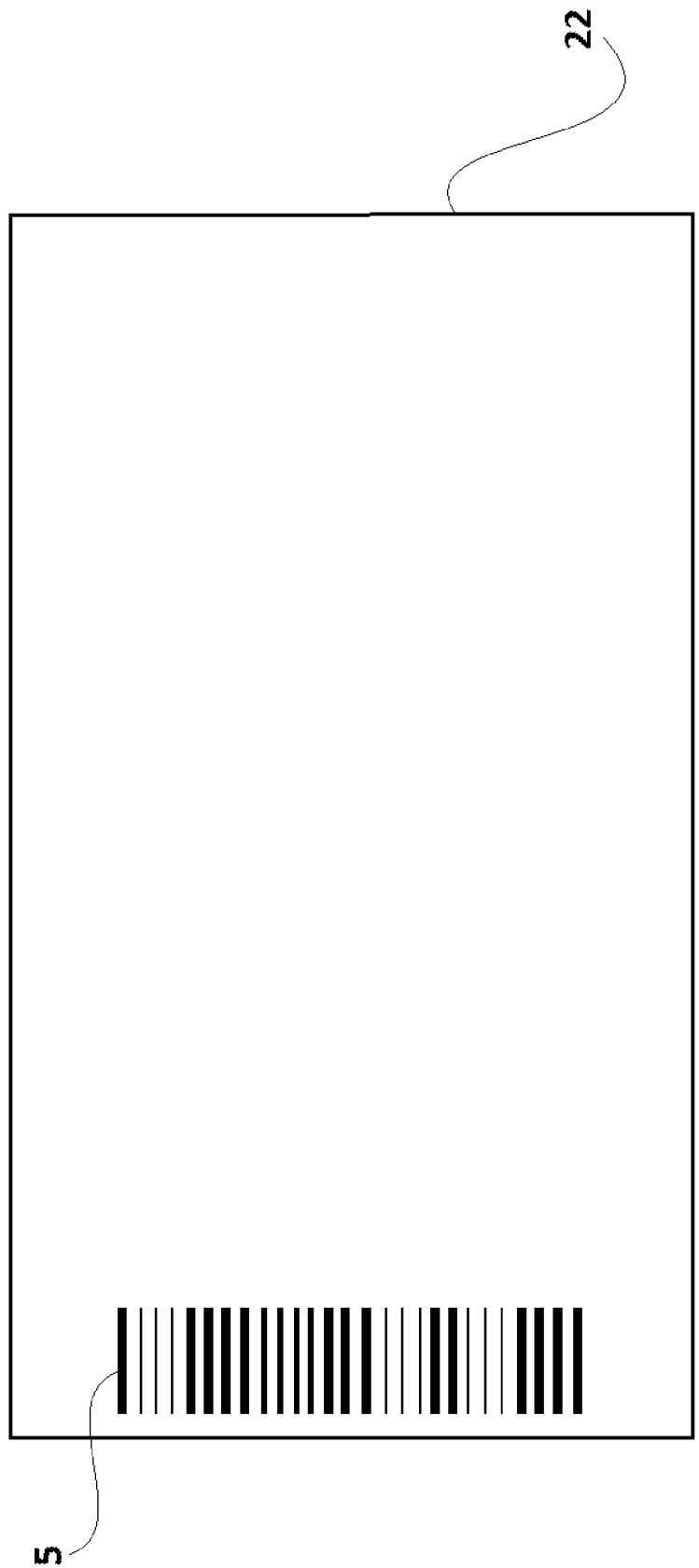
FIG. 5F illustrates a plan view of the inner side of the cover layer.
Figure 6:
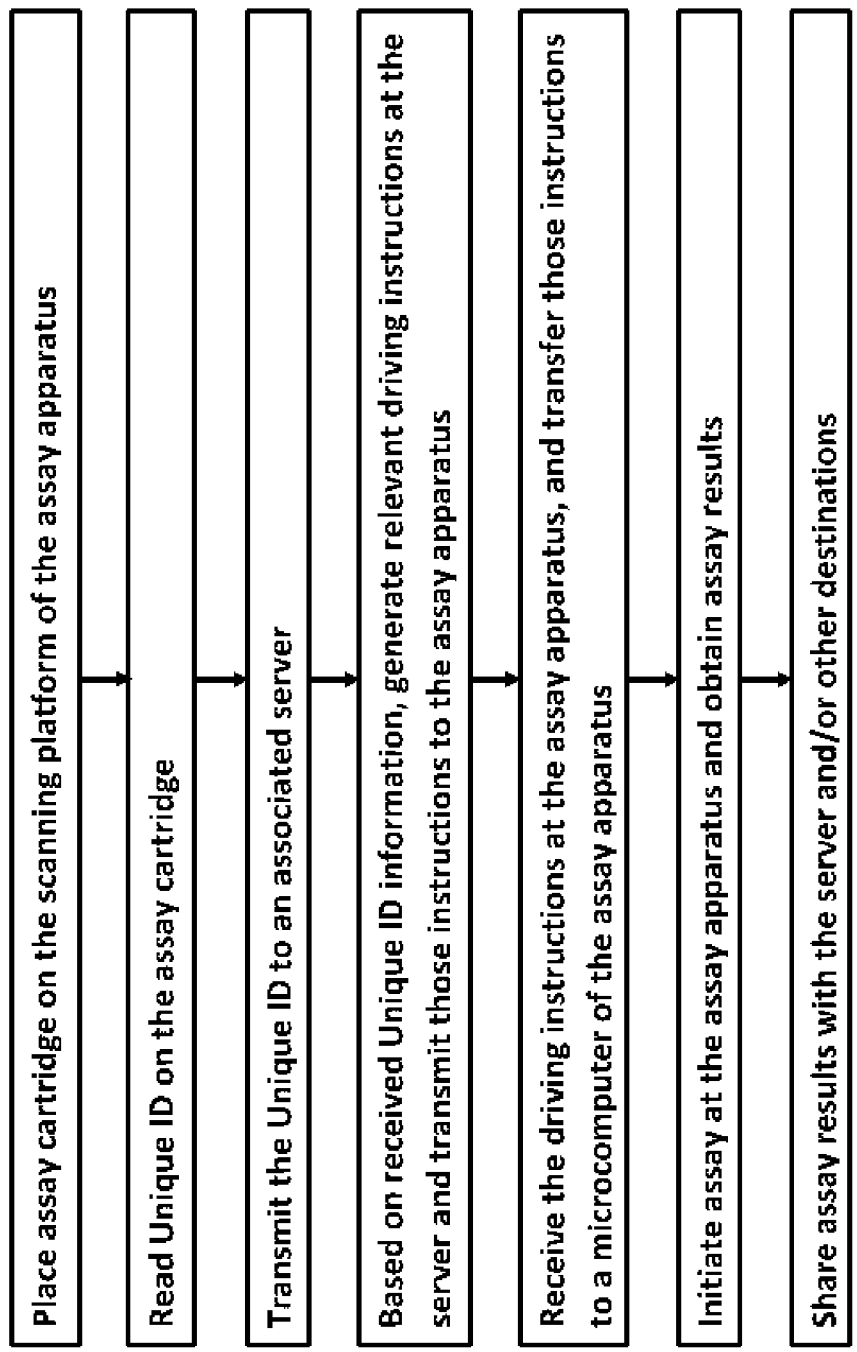
FIG. 6 is a flow diagram of the steps involved in initiating and performing an assay with the assay driving apparatus and the assay cartridge shown and described herein.
Figure 7:
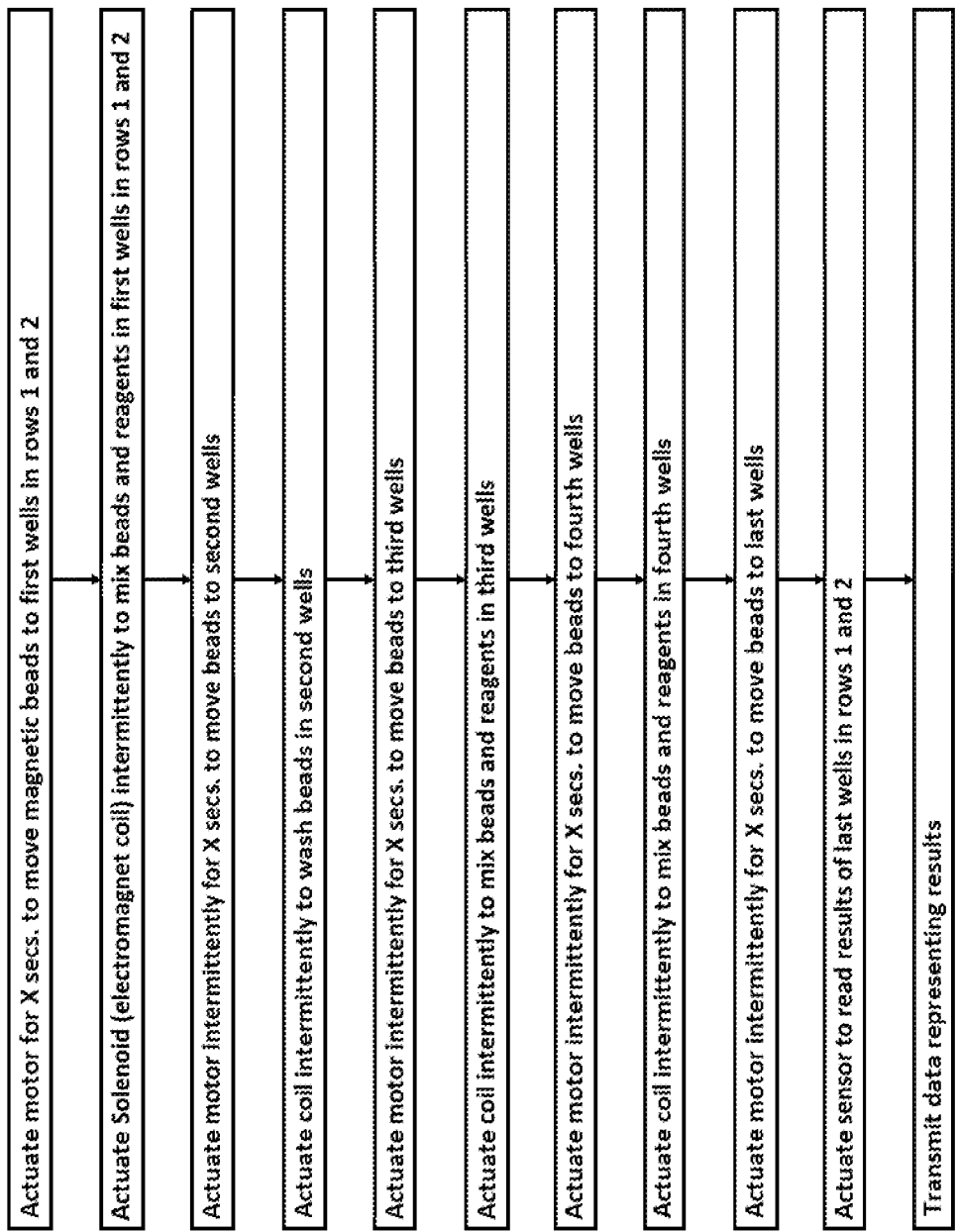
FIG. 7 is a flow diagram of the instructions for initiating and performing an assay with the assay driving apparatus and the assay cartridge shown and described herein.

Prior to using cartridge 10 in an assay, one scans code 5 and sends the information to a server/website, which identifies the assay and provides the instructions about the assay steps and their timing (preferably over the internet) to a microcomputer which controls movement of magnet holder 138 (FIGS. 6 and 7). Referring to FIGS. 4A to 4C, magnetic holder 138 is preferably a polymer which carries spherical magnets 218 and, optionally, in the embodiment in FIG. 4B, orienting magnets 220, which align the polarity of spherical magnets 218. Alternatively, the instructions can be retrieved from the server/website and manually input or electronically fed into the microcomputer.

A variety of shapes, sizes and materials can be used to construct the cartridge 10 or 11 itself. Considerations for the materials used in such cartridges include that it should be substantially transparent, so as to allow the inner side of the cover 22 (with code 5) to be viewed from one side, and so that the inner side of cover 22 (preferably white or another suitable background color) can be imaged by scanning. Alternatively, cartridge 10 or 11 itself could be colored for assay contrast and encoded with code 5, or layer 20 could be colored or otherwise opaque to provide a background for imaging.

Suitable materials for cartridge 10 or 11 include polystyrene, polytetrafluoroethylene ("Teflon®") and polyethylene. Reagent solutions in different portions of the capillary are kept separated and discontinuous by air gaps 18.

Wells 12, 13, 14, 15 are covered with layer 20, and then it's covered by cover 22, as described above.

Heating and Melting of Hydrogel

The reagents and magnetic beads may then be preloaded in the wells 12, 13, 14, 15, preferably being placed (by pipette or capillary action) into the mini-holes 16 in each of wells 12, 13, 14, 15. The reagents and magnetic beads are preferably in a solution including a gelatin hydrogel, which assists in sealing the contents of wells 12, 13, 14, 15 from the open channels 18. Wells 12, 13, 14, 15 are preferably covered with layer 20, and then with cover 22, as described above.

In a preferred procedure, a solution including the gel reagents, capable of forming a hydrogel, is first preferably heated sufficiently to dissolve any gel which forms. The solution is then cooled sufficiently (e.g., 37° C.) where one can add beads, antibodies or other reagents, without significant risk of denaturation or damage. The solution is then added to the wells in cartridge 10 or 11, along with magnetic beads and other assay reagents in appropriate well(s) 12, 13, 14, 15, and then preferably cooled to congealing, e.g., about 4° C. The loaded and sealed cartridge 108 (FIG. 5A) can be stored and shipped, preferably with the temperature held at 4° C. during shipping, or, provided the temperature in shipping remains below the hydrogel solution melting point, it can be shipped at a higher temperature (e.g., up to RT). As long as the hydrogel remains congealed, the reagent solutions and magnetic beads will be held in the wells in which they were placed, and will not tend to migrate into other wells.

Before the assay is used, the sealed cartridge 108 is heated to 37° C. to melt the hydrogel solution. The assay can be run at 37° C., or it might be cooled to RT—provided the hydrogel remains liquid and does not congeal.

In no case should sealed cartridge 10 be heated as high as the melting temperature of the paraffin in layer 20—otherwise, layer 20 will melt into the wells.

One preferred method to monitor the temperature is by placing color-changing thermachromic pigments (available from SolarColorDust.com) in the wells containing solution; and a more preferred method is to incorporate or coat the pigments onto beads, which are placed in the wells. The pigment can be incorporated into or coated onto non-magnetic beads or microbeads, or can be incorporated into or coated onto magnetic beads (a core-shell bead with a magnetic core and a pigment-dyed polymer shell is one embodiment); collectively, these are referred to hereinafter as "Pigmented Beads". In the latter case, these magnetic beads are different from the magnetic beads used to carry the ELISA reagent such as a capture antibody.

Examples of using a cartridge of the invention for an assay are below.

Example 1

Using the Cartridge to Perform an Assay

A ready-to-use assay kit is prepared by sealing cartridge 10 or 11 with layer 20 and cover 22 (forming sealed cartridge 108), and pre-filling it with reagents and magnetic beads, and including hydrogel and Pigmented Beads, as described above. The cartridge 108 is aligned so cover 22 is down and so that the magnetic beads rest on the inner surface of layer 20.

The degree of heating needed to melt the hydrogel can be controlled, to prevent reagents and coverings on cartridge 108 from exceeding a limit—that limit preferably being well below the temperature at which assay performance may be affected. During heating, therefore, where Pigmented Beads are in use, one monitors the Beads' color, by viewing through a microscope, or using a scanner. Heating is stopped when a color change indicating melting is observed. Alternatively, one can include an additional pigment or pigments in the Pigmented Beads which change color to indicate that assay performance may be affected, assay reagents may be affected, or components of the cartridge 108 may melt, if the temperature continues to rise.

One system to perform stopping heating, is to make color-change the control element for a thermostat—such that after heating commences cartridge 108 is observed with a scanner, which, when it detects a color change indicating a target temperature, sends a signal to a microprocessor, whereby power to the heater is cut. At that point, the temperature of the solution is such that it is liquefied and the assay can commence, as described below.

In an alternative embodiment, a constant power level is provided to the heating element during the assay such that at equilibrium, the cartridge temperature is within the range suitable for conducting the assay. In this case, once color change is observed by a scanner to indicate reagents have reached a temperature within the desired range, the microprocessor instructs the device to begin the assay sequence.

Alternatively, the heating of the hydrogel can be carried out in a separate vessel during the sealing of cartridge 108, and the temperature monitored with Pigmented Beads as described above. Once at a suitable temperature, the hydrogel is added to the wells.

If at any point during the assay, the temperature falls below a limit (as preferably indicated by a third color change in the Pigmented Beads) the scanner can again send a signal to a microprocessor, this time to cause heating of cartridge 108. It is noted that one generally should not excessively heat cartridge 108, but some heat may be provided to maintain the temperature at an appropriate level below the excessive threshold.

The magnetic beads are induced to travel from wells 12, 13 to other wells 14, 15 through channels 18 by moving the holder 138 (and magnets 218) in the direction of travel—magnetic beads are drawn towards the magnets 218. The magnetic beads can also be moved so as to mix magnetic beads and reagents by, for example, moving the magnets 218 in a different direction from the direction of travel, e.g., so as to induce the magnetic beads to move back and forth inside one or more of the wells 12, 13, 14, 15.

The movement of the magnetic beads in preferred embodiments is designed to prevent clumping of the magnetic beads and instead move the beads while maintaining a bead distribution approaching or achieving a single layer over the inner side of layer 20. In one embodiment, mixing of the beads with the contents of a well is by movement of the beads transversely to the direction of travel in an oscillating manner. The mixing can also be by oscillating holder 138 in any direction, whether the same or different from the direction of travel.

Example 2

Using the Cartridge to Perform an ELISA Immunoassay

After cartridge 10 or 11 is loaded with magnetic antibody-coated beads (preferably, in the wells 14 and 15 nearest wells 12, 13, as noted above) and reagents suitable for an ELISA are loaded in other wells 14, 15, sample is added to well 12, and a control is added to well 13. In some cases, the control may be pre-loaded along with the magnetic beads and ELISA reagents. The instructions are executed to induce assay driver to move holder 138 such that the antibody-coated magnetic beads are moved through channels 18, first to wells 12, 13, and then through wells 14, 15, in sequence. The antibody coating on the beads binds to reactive antigens in the sample or control which reactive antigens are then carried by the beads.

Oscillating movement of holder 138 in a direction the same, different or transverse to the direction of travel can be carried out in certain wells, or in all wells in the series, to mix their contents.

It is preferred the strength of the magnetic field acting on magnetic beads and of the acceleration and deceleration of holder 138 is adjusted so that the beads spread out somewhat (like a comet tail) when oscillating holder 138 to mix beads with the well contents. Optimization of the movement parameters of holder 138 to achieve rapid mixing of beads and well contents is therefore preferred.

Some wells 14, 15, in the series are loaded with detection antibodies carrying enzyme, or preferably, also with secondary antibodies carrying enzyme. Ultimately, the beads are moved to those wells 14, 15 containing the substrate for the enzyme carried by the detection or secondary antibodies, which induces a detectable color change. The color change can be accomplished with an enzyme substrate combination. In such case, the wells where there is a color change may contain one of the following: PNPP (p-Nitrophenyl Phosphate), ABTS (2,2'-Azinobis [3-ethylbenzothiazoline-6-sulfonic acid]-diammonium salt), OPD (o-phenylenediamine dihydrochloride), or TMB (3,3',5,5'-tetramethylbenzidine)]. One suitable enzyme-substrate combination is horseradish peroxidase (HRP) as the enzyme and TMB as the detection substrate. When using chemiluminescent chemicals and HRP, which is another option, light is generated as well as a color change.

Some wells 14, 15 may optionally serve as wash chambers to remove contaminants attached non-specifically to the beads—although contaminants on the beads are also removed by passage through the air gaps in channels 18. Oscillating movement of holder 138 in other directions can enhance washing the contents of wells which contain wash reagents—when the beads reside in those wells.

The concentration of analyte in sample or control solution is proportional to the amount of the analyte that gets attached to the antibody-coated magnetic particles, which in turn is proportional to the number of detection antibody molecules that get attached to the analyte. Because the detection or secondary antibodies are attached to HRP, the quantity of detection or secondary antibodies bound to HRP governs the rate of catalytic conversion of TMB.

The color concentration can be quantified with a light source and detector, for example. The final wells can be scanned and either imaged or otherwise quantified for color change, and the representative data can be transmitted for remote analysis of the assay results, or to the patient or a designated recipient, as described further below. A suitable scanner for generating the assay well images is a four channel photoelectric color sensor, capable of sensing the total light signal and up to three color-filtered signals.

Example 3

Remote Assay Authorization, Performance and Reporting

The assay cartridge 10 or 11 and the system described herein is for use with an automated assay driver, which actuates and controls performance of the assay in a secure remotely authorized system. After the assay cartridge 10 or 11 is authenticated (through reading the code 5 and transmitting it to a secure server or website), instructions are transmitted to the assay driver, which then controls movement of holder 138 in designated directions at designated times, to perform the assay. After the assay is completed, representations of the assay results (from the wells where color change took place) are sent from the site of the assay performance for results analysis through the secure system, and/or to a health care worker, and/or to the subject of the assay and/or to his/her designees (including distribution to anyone who can receive the material under applicable HIPAA regulations). The flow of steps in the authentication and assay process is depicted in FIGS. 6 and 7.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An assay device stable for shipment comprising: a plurality of wells which are a series of openings connected with first channels in a first surface of the body of the assay device, wherein:
   (i) said wells house assay reagents in solution and the first channels include an air gap to separate fluids in the wells,
   (ii) the wells include a gelatin hydrogel of at least 150 Bloom with a melting temperature above room temperature and a gelling temperature above 10° C., wherein when gelled, the hydrogel interfaces with air in the air gap and prevents movement of all assay reagents from the wells into the air gap, and
   (iii) the wells are sealed using a plastic film covering substantially the first surface.

2. The device of claim 1 wherein the gelatin hydrogel is less than 10% gelatin.

3. The device of claim 1 wherein the gelatin hydrogel is Bloom range 180-200.

4. The device of claim 1 wherein the gelatin hydrogel is at a concentration range of 1 to 4%.

5. The device of claim 1 wherein the air gap is formed by second channels providing access from outside of the assay device to the interior of the first channels.

6. The device of claim 5 wherein the second channels extend from the first surface through the body to its opposite surface.

7. The device of claim 1 wherein the plastic film is adhered to substantially flat portions of said first surface.

8. The device of claim 1 further including encoding the cartridge with a QR or other code.

9. The device of claim 7 further including adhering a paper or polymer layer substantially covering said plastic film.

10. The device of claim 9 further including a QR or other code imprinted on the inner side of the paper or polymer layer.

11. The device of claim 9 wherein the plastic paraffin film and the paper or polymer layer combined thickness is about 100 to 500 microns.

12. The device of claim 7 wherein the substantially flat portions of said first surface have a gritty finish.

13. The device of claim 12 wherein said substantially flat portions have a 600 grit finish.

14. The device of claim 12 wherein said substantially flat portions have a SPI B-1 grade finish.

15. The device of claim 1 wherein the body is formed of polystyrene, polytetrafluoroethylene ("Teflon®") or polyethylene.

16. The device of claim 1 wherein the melting temperature of the hydrogel is about 37° C.

17. The device of claim 1 wherein the plastic film is paraffin film.

* * * * *